United States Patent
Waffler (10) Patent No.: US 10,652,989 B2
(45) Date of Patent: May 12, 2020

(54) CIRCUIT ARRANGEMENT (71) Applicant: Siemens Healthcare GmbH, Erlangen (DE)

(72) Inventor: Stefan Waffler, Buckenhof (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/385,057

(22) Filed: Apr. 16, 2019

(65) Prior Publication Data

US 2019/0327822 A1    Oct. 24, 2019

(30) Foreign Application Priority Data

Apr. 23, 2018 (EP) .................................. 18168791

(51) Int. Cl.
| | |
|---|---|
| *H05G 1/10* | (2006.01) |
| *A61B 6/03* | (2006.01) |
| *H01F 27/28* | (2006.01) |
| *H01J 35/02* | (2006.01) |

(52) U.S. Cl.
CPC .............. *H05G 1/10* (2013.01); *A61B 6/03* (2013.01); *H01F 27/28* (2013.01); *H01J 35/025* (2013.01)

(58) Field of Classification Search
CPC ... H05G 1/10; A61B 6/03; H01F 27/28; H01J 35/02; H01J 35/025
USPC ......................................................... 378/101
See application file for complete search history.

(56) References Cited

U.S. PATENT DOCUMENTS

| 4,481,654 A | 11/1984 | Daniels et al. | |
|---|---|---|---|
| 5,123,038 A | 6/1992 | Negle et al. | |
| 5,894,502 A * | 4/1999 | Beyerlein ................ | H05G 1/10 378/101 |

(Continued)

FOREIGN PATENT DOCUMENTS

DE        3929888 A1    3/1991

OTHER PUBLICATIONS

Extended European Search Report and English translation thereof dated Oct. 19, 2018.

(Continued)

*Primary Examiner* — Jurie Yun
(74) *Attorney, Agent, or Firm* — Harness, Dickey & Pierce, P.L.C.

(57) ABSTRACT

A circuit arrangement includes an X-ray tube, including a cathode and an anode, and a high-voltage transformer. In an embodiment, the high-voltage transformer includes at least one primary winding, at least one first secondary winding, including a first oscillating circuit, wherein the first oscillating circuit includes a first leakage inductance and a first winding capacitance, to adjust a first resonance frequency, and at least one second secondary winding, including a second oscillating circuit, wherein the second oscillating circuit includes a second leakage inductance and a second winding capacitance, to adjust a second resonance frequency, the first resonance frequency matching the second resonance frequency, the first winding capacitance and the second winding capacitance differing in value and the first leakage inductance and the second leakage inductance differing in value. The first secondary winding is electrically connected to the cathode and the second secondary winding is electrically connected to the anode.

20 Claims, 4 Drawing Sheets

(56) References Cited

U.S. PATENT DOCUMENTS 7,400,708 B2 * 7/2008 Takahashi ............... H05G 1/10
378/101

OTHER PUBLICATIONS

European Intention to Grant and English translation thereof dated Nov. 27, 2019.
European Search Report (EPA Form 1507N) for European Application No. EP18168791 dated Oct. 19, 2018.

* cited by examiner

CIRCUIT ARRANGEMENT

PRIORITY STATEMENT

The present application hereby claims priority under 35 U.S.C. § 119 to European patent application number EP 18168791.4 filed Apr. 23, 2018, the entire contents of which are hereby incorporated herein by reference.

FIELD

Embodiments of the application generally relates to a circuit arrangement, to an X-ray unit and to a computed tomography unit.

BACKGROUND

High-voltage transformers are typically used to supply an X-ray tube with high voltage. On a cathode side, the high-voltage transformer supplies, for example, a negative high voltage, relative to a ground potential, and on an anode side, a positive high voltage, relative to the ground potential. In particular, a high voltage resulting therefrom between an anode of the X-ray tube and a cathode of the X-ray tube accelerates electrons emitted from the cathode, which conventionally strike the anode and are decelerated in the process, whereby, in particular, X-ray radiation is produced for imaging. However, a certain proportion of the emitted electrons is typically scattered back at the anode.

The back-scattered electrons are captured for example by a grounded metal central part of the X-ray tube, so that, in particular, a differential current is adjusted in the X-ray tube. Therefore the X-ray tube acts in particular as an asymmetric load. Due to the differential current of the X-ray tube, the high-voltage transformer is typically asymmetrically loaded on the anode side and on the cathode side in relation to a respective load current. In other words, a differential current of the high-voltage transformer is adjusted between the anode side and the cathode side, and this is proportional to the differential current of the X-ray tube.

Typically, the differential current of the X-ray tube therefore correlates with the differential current of the high-voltage transformer. The differential current of the high-voltage transformer is produced in particular in that the load current on the anode side and the load current on the cathode side differ, in particular are asymmetric. In this case a voltage asymmetry typically follows at the high-voltage transformer. However, a conventional high-voltage transformer is conventionally symmetrical in design, for which reason the voltage asymmetry can be adjusted at the conventional high-voltage transformer due to the differential current of the X-ray tube. The voltage asymmetry follows in particular from the fact that in particular different high voltages are adjusted at the anode side and the cathode side. Due to the voltage asymmetry the high-voltage transformer and/or the X-ray tube can incur damage. Furthermore, the quality of imaging can be reduced if the high-voltage transformer for the X-ray tube is used during imaging.

Two high-voltage transformers that are independent of each other are therefore conventionally used, it being possible to prevent the voltage asymmetry by way of independent control of the cathode-side and anode-side high voltages. Production and maintenance costs increase considerably as a result because, typically, even further multiple units, in particular high-voltage inverters and/or associated oscillating circuit throttles, also have to be installed due to the two high-voltage transformers.

An alternative possibility is use of a medium-voltage transformer with high-voltage cascade connected downstream, so that a complexity of a circuit arrangement having the medium-voltage transformer, the high-voltage cascade and the X-ray tube, and therewith likewise the costs, increase.

U.S. Pat. No. 4,481,654 A discloses a high-voltage transformer comprising two transformers having matching resonance frequency.

SUMMARY

Embodiments of the invention disclose a circuit arrangement, an X-ray unit and a computed tomography unit, in which a voltage asymmetry is reduced due to an asymmetric load.

Advantageous embodiments are described in the claims.

Depending on the design, deviations from the specifications in an ideal environment can result with electronic circuits or components in a real environment. Where mention is made hereinafter of matching, correspondence, uniformity of construction etc., then this wording primarily refers to a definition or dimensioning of the circuit or the component in the ideal environment. Deviations can nevertheless occur in the real environment although this deviation in the circuit or component is typically not intended. The ideal environment can be for example software for designing a high-voltage transformer.

An embodiment of the inventive circuit arrangement comprises:
an X-ray tube, which has a cathode and an anode, and
a high-voltage transformer, which
has at least one primary winding,
at least one first secondary winding, which has a first oscillating circuit, wherein the first oscillating circuit has a first leakage inductance and a first winding capacitance, which together adjust a first resonance frequency, and
at least one second secondary winding, which has a second oscillating circuit, wherein the second oscillating circuit has a second leakage inductance and a second winding capacitance, which together adjust a second resonance frequency,
wherein the first resonance frequency and the second resonance frequency match,
wherein the first winding capacitance and the second winding capacitance differ in value and
wherein the first leakage inductance and the second leakage inductance differ in value,
characterized in that
the at least one first secondary winding is electrically connected to the cathode and
the at least one second secondary winding is electrically connected to the anode.

An embodiment of the inventive X-ray unit hincludes an embodiment of the circuit arrangement. A production time of the X-ray unit with the high-voltage transformer is advantageously shorter, because, typically, only the high-voltage transformer has to be produced in order to reduce the voltage asymmetry.

An embodiment of the inventive computed tomography unit comprises the X-ray unit. The computed tomography unit is preferably smaller compared to a conventional computed tomography unit having two conventional high-voltage transformers connected in parallel. The computed tomography unit is typically less expensive to produce because the asymmetric load is preferably connected to the asymmetric high-voltage transformer.

The invention will be described and explained in more detail below with reference to the example embodiments illustrated in the figures. Basically, structures and units that remain essentially the same are designated with the same reference numerals in the following description of the figures as in the case of the first occurrence of the respective structure or unit.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the inventive circuit arrangement comprises:

an X-ray tube, which has a cathode and an anode, and
a high-voltage transformer, which
has at least one primary winding,
at least one first secondary winding, which has a first oscillating circuit, wherein the first oscillating circuit has a first leakage inductance and a first winding capacitance, which together adjust a first resonance frequency, and
at least one second secondary winding, which has a second oscillating circuit, wherein the second oscillating circuit has a second leakage inductance and a second winding capacitance, which together adjust a second resonance frequency,
wherein the first resonance frequency and the second resonance frequency match,
wherein the first winding capacitance and the second winding capacitance differ in value and
wherein the first leakage inductance and the second leakage inductance differ in value,
characterized in that
the at least one first secondary winding is electrically connected to the cathode and
the at least one second secondary winding is electrically connected to the anode.

The high-voltage transformer, in particular the circuit arrangement, in particular provides the following advantages: an asymmetric load, in particular the X-ray tube, can be operated with a high voltage generated via the high-voltage transformer. A voltage asymmetry can be advantageously reduced by way of the high-voltage transformer alone, so that maintenance expenditure of the high-voltage transformer preferably works out to be less. Preferably, measurement data having a high image quality can be acquired during imaging by way of the reduction in the voltage asymmetry if the high-voltage transformer is used during imaging. The voltage asymmetry is preferably reduced without additional components, which should typically balance the asymmetric load.

The high-voltage transformer is advantageous in particular because the high-voltage transformer typically has a higher power density compared to two conventional symmetrical high-voltage transformers connected in parallel.

Advantageously, by matching the first resonance frequency and the second resonance frequency, the voltage asymmetry over an operating frequency range, in particular of a resonance converter used for high-voltage generation, can be kept low.

One embodiment provides that a first load current is adjusted in the at least one first secondary winding, wherein a second load current is adjusted in the at least one second secondary winding, wherein the first load current differs from the second load current by a differential current of the high-voltage transformer, which is proportional to a differential current of the X-ray tube. The differential current of the high-voltage transformer, in particular the first load current and the second load current is preferably dimensioned in such a way that the voltage asymmetry at the high-voltage transformer is reduced. The cathode-side high voltage and the anode-side high voltage particularly advantageously match in value, preferably despite the asymmetric load, in particular despite the differential current of the X-ray tube. The high-voltage transformer therefore preferably balances the voltage asymmetry. The high-voltage transformer is advantageously designed as a function of the asymmetric load, in particular of the X-ray tube. The high-voltage transformer therefore provides the advantage of an individual adjustment to the asymmetric load.

One embodiment provides that the at least one primary winding forms a first cylinder having a first longitudinal axis, wherein the at least one first secondary winding and the at least one second secondary winding together form a second cylinder having a second longitudinal axis, wherein the first longitudinal axis is parallel to the second longitudinal axis and wherein the first cylinder is arranged offset relative to the second cylinder along the first longitudinal axis. The offset arrangement of the first cylinder relative to the second cylinder is advantageous in particular because a corresponding structural measure can be easily carried out. Advantageously, the leakage inductances can be precisely adjusted by way of this embodiment.

One embodiment provides that a winding wire of the at least one first secondary winding differs from a winding wire of the at least one second secondary winding according to at least one parameter from the following list:
a thickness of the winding wire,
a thickness of an enamel insulation layer of the winding wire,
an dielectric constant of the enamel insulation layer of the winding wire. A variation in an embodiment of the winding wires of the at least one first secondary winding from an embodiment of the winding wires of the at least one second secondary winding is advantageous because this variation can be carried out several times. Preferably, the at least one first secondary winding and/or the at least one second secondary winding can be easily exchanged. Advantageously, the winding capacitances can be precisely adjusted by way of this embodiment.

One embodiment provides that a first diameter of the at least one first secondary winding is smaller than a second diameter of the at least one second secondary winding, so that the first leakage inductance is smaller than the second leakage inductance. A magnitude of the high-voltage transformer can be advantageously reduced by using different diameters. Interconnection of an additional oscillating circuit throttle for adjusting the inductance with the high-voltage transformer can be advantageously dispensed with in this way, furthermore, so that costs and installation space are saved. Advantageously, the leakage inductances can be precisely adjusted by way of this embodiment.

One embodiment provides that the high-voltage transformer has a primary coil body and a secondary coil body, wherein the secondary coil body has a first secondary coil half and a second secondary coil half, wherein the first secondary coil half has the at least one first secondary winding, wherein the second secondary coil half has the at least one second secondary winding and wherein the first secondary coil half and the second secondary coil half are constructed asymmetrically to each other. The high-voltage transformer can preferably operate the asymmetric load without a further high-voltage transformer being connected to the asymmetric load. In other words, the high-voltage transformer is an asymmetric high-voltage transformer, which is designed for an asymmetric load, in particular the X-ray tube. Since, typically, only the high-voltage transformer without the further high-voltage transformer is provided for operation of the X-ray tube, the costs and installation space are reduced. A degree of asymmetry of the asymmetric load, in particular of the X-ray tube, can be advantageously determined, with the high-voltage transformer thereafter preferably being designed according to the degree of asymmetry. In other words, the degree of asymmetry is typically determined and/or measured in a laboratory environment and then the high-voltage transformer is adapted to the asymmetric load in such a way that the voltage asymmetry is reduced.

One embodiment provides that the at least one first secondary winding is arranged in a first chamber of the first secondary coil half together with at least one first paper insulation layer, wherein the at least one second secondary winding is arranged in a second chamber of the second secondary coil half together with at least one second paper insulation layer and wherein an arrangement of the first paper insulation layer relative to the at least one first secondary winding differs from an arrangement of the second paper insulation layer relative to the at least one second secondary winding. Advantageously, any arrangement of the paper insulation layer can be easily adapted to the asymmetric load. Advantageously, the winding capacitances can be precisely adjusted by way of this embodiment.

One embodiment provides that the at least one first secondary winding is arranged in a first chamber of the first secondary coil half, wherein the at least one second secondary winding is arranged in a second chamber of the second secondary coil half and wherein a first width of the first chamber is greater than a second width of the second chamber, so that the first winding capacitance is greater than the second winding capacitance. This embodiment offers the advantage, in particular, that this structural measure, namely the variation in the width of the chambers, preferably enables a robust high-voltage transformer. Advantageously, the winding capacitances can be precisely adjusted by way of this embodiment.

One embodiment provides that the first diameter of the at least one first secondary winding is smaller than the second diameter of the at least one second secondary winding and that the first width of the first chamber is greater than the second width of the second chamber. Advantageously, the first resonance frequency and the second resonance frequency match although the first winding capacitance and the second winding capacitance and also the first leakage inductance and the second leakage inductance differ in value. Advantageously, the winding capacitances and the leakage inductances can be precisely adjusted by way of this embodiment.

The circuit arrangement provides the advantage, in particular, that the, in particular asymmetric, high-voltage transformer, can be electrically connected to the X-ray tube, acting in particular as an asymmetric load, enabling operation of the X-ray tube via the high-voltage transformer.

One embodiment provides that the X-ray tube has a metal central part and that the differential current of the X-ray tube is adjusted between the anode and the metal central part. This embodiment provides the advantage that the voltage asymmetry at the high-voltage transformer turns out to be low despite the electrons scattered back at the anode.

One embodiment provides that at least one oscillating circuit throttle is interconnected between the high-voltage transformer and the X-ray tube. This embodiment provides the advantage in particular that the high-voltage transformer is smaller if the at least one oscillating circuit throttle is additionally arranged outside of the high-voltage transformer.

One embodiment provides that at least one capacitor is interconnected between the high-voltage transformer and the X-ray tube. This embodiment provides the advantage in particular that the high-voltage transformer is smaller if the at least one capacitor is additionally arranged outside of the high-voltage transformer.

An embodiment of the inventive X-ray unit has a circuit arrangement. A production time of the X-ray unit with the high-voltage transformer is advantageously shorter, because, typically, only the high-voltage transformer has to be produced in order to reduce the voltage asymmetry.

An embodiment of the inventive computed tomography unit comprises the X-ray unit. The computed tomography unit is preferably smaller compared to a conventional computed tomography unit having two conventional high-voltage transformers connected in parallel. The computed tomography unit is typically less expensive to produce because the asymmetric load is preferably connected to the asymmetric high-voltage transformer.

Figure 1:
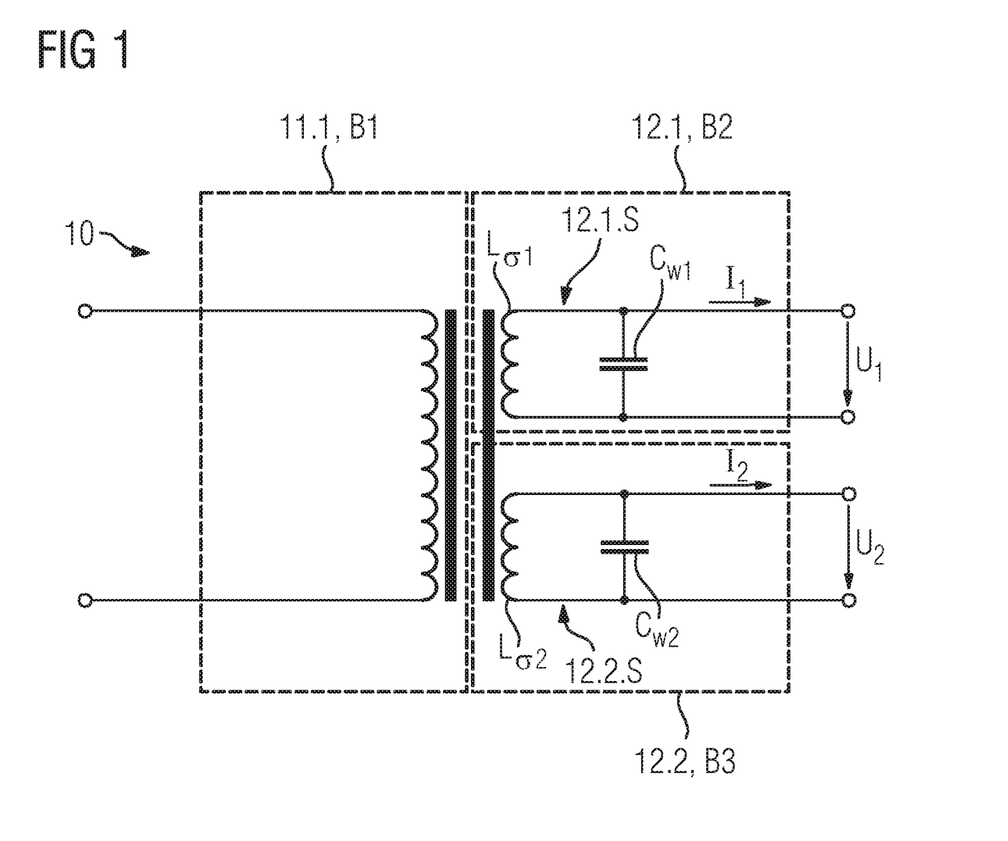
FIG. 1 shows an equivalent circuit diagram of a high-voltage transformer in a first example embodiment.

FIG. 1 shows a high-voltage transformer 10 for an X-ray tube 20, which is not shown in FIG. 1, in an equivalent circuit diagram. The high-voltage transformer 10 has at least one primary winding 11.1, at least one first secondary winding 12.1 and at least one second secondary winding 12.2. The high-voltage transformer 10 can have further elements which are not shown in FIG. 1.

The high-voltage transformer 10 is depicted in the equivalent circuit diagram as a real high-voltage transformer. The high-voltage transformer 10 is typically an asymmetric high-voltage transformer.

The equivalent circuit diagram of the high-voltage transformer 10 is divided in FIG. 1 into three regions B1, B2, B3, with the three regions B1, B2, B3 each being bordered by broken lines. Equivalent circuits of the at least one primary winding 11.1, the at least one first secondary winding 12.1 and the at least one second secondary winding 12.2 are depicted in the three regions B1, B2, B3.

The at least one first secondary winding 12.1 has a first oscillating circuit 12.1.S, wherein the first oscillating circuit 12.1.S has a first leakage inductance $L_{o1}$ and a first winding capacitance $C_{W1}$, which together adjust a first resonance frequency.

The at least one second secondary winding 12.2 has a second oscillating circuit 12.2.S, wherein the second oscillating circuit 12.2.S has a second leakage inductance $L_{o2}$ and a second winding capacitance $C_{W2}$, which together adjust a second resonance frequency.

The first resonance frequency and the second resonance frequency match. In other words, the first resonance frequency and the second resonance frequency correspond in value. The first winding capacitance $C_{W2}$ and the second winding capacitance $C_{W2}$ differ in value and the first leakage inductance $L_{o1}$ and the second leakage inductance $L_{o2}$ differ in value.

A first load current I1 is adjusted in the at least one first secondary winding 12.1 and a second load current I2 is adjusted in the at least one second secondary winding 12.1, in particular if the high-voltage transformer 10 is connected to an asymmetric load. In other words, the first load current I1 flows in the first secondary winding 12.1 and the second load current I2 flows in the second secondary winding 12.2. Adjusting the first load current I1 and/or the second load current I2 typically means that the high-voltage transformer 10 is stressed by operation of a load, in particular the asymmetric load. When the first load current I1 is adjusted, a first high voltage U1 typically drops across the at least one first secondary winding 12.1. When the second load current I2 is adjusted, a second high voltage U2 typically drops across the at least one second secondary winding 12.2. The first high voltage U1 and the second high voltage U2 are typically alternating voltages.

If the load is the asymmetric load, for example the X-ray tube 20, the first high voltage U1 preferably matches the second high voltage U2 in value, with the first load current I1 differing from the second load current I2 in value. In this case a voltage asymmetry at the high-voltage transformer 10 is preferably lower as a result, particularly preferably avoided, because the first resonance frequency and the second resonance frequency match, the first winding capacitance $C_{W1}$ and the second winding capacitance $C_{W2}$ differ in value and because the first leakage inductance $L_{o1}$ and the second leakage inductance $L_{o2}$ differ in value. In other words, the high-voltage transformer 10 is preferably the asymmetric high-voltage transformer, wherein, during operation with the asymmetric load, in particular with the X-ray tube 20, the voltage asymmetry is lower compared to if the high-voltage transformer 10 is a conventional symmetric high-voltage transformer.

The first load current I1 differs from the second load current I2, in particular in value, by a differential current 10.IΔ of the high-voltage transformer 10. The differential current 10.IΔ of the high-voltage transformer 10 is typically an alternating current.

The differential current 10.IΔ of the high-voltage transformer 10 is proportional to a differential current 20.IΔ of the X-ray tube 20, which is typically a direct current. In other words, the differential current 20.IΔ of the X-ray tube 20 correlates with the differential current 10.IΔ of the high-voltage transformer 10. A rectified mean of the differential current 10.IΔ of the high-voltage transformer 10 and a value of the differential current 20.IΔ of the X-ray tube 20 differ, for example, by a factor of 0 to 10, particularly advantageously by a factor of 2 to 3.

The differential current 10.IΔ of the high-voltage transformer 10 is typically generated in that the first winding capacitance CW1 and the second winding capacitance CW2 and also the first leakage inductance Lσ1 and the second leakage inductance Lσ2 differ in value, with the first resonance frequency and the second resonance frequency matching. The first load current I1 is typically higher, the smaller the first leakage inductance Lσ1 is. Alternatively or additionally, the first load current I1 is higher, the greater the first winding capacitance CW1 is, in particular if the first resonance frequency and the second resonance frequency match.

In one example embodiment the differential current 20.IΔ of the X-ray tube 20 is adjusted in the X-ray tube 20. In other words, the differential current 20.IΔ of the X-ray tube 20 preferably flows off in the X-ray tube 20. Particularly advantageously, the electrons scattered back on an anode 22 of the X-ray tube 20 match the differential current 20.IΔ of the X-ray tube 20 in value. In other words, the differential current 20.IΔ of the X-ray tube 20 preferably comprises the electrons scattered back at the anode 22 of the X-ray tube 20. The back-scattering of the electrons at the anode 22 can comprise rebounding at the anode 22. The differential current 20.IΔ of the X-ray tube 20 can comprise further electrons which did not previously strike the anode 22 but are typically scattered directly from the cathode 21 to the metal central part 23. The differential current 20.IΔ of the X-ray tube 20 typically comprises less than 20%, in particular less than 10%, of all electrons emitted by the cathode 21.

The differential current 20.IΔ of the X-ray tube 20 can be designated as a leakage current and/or parasitic current. Basically it is conceivable for a number of electrons scattered back at the anode 22 of the X-ray tube 20 to vary in such a way that the high-voltage transformer 10, in particular the asymmetric high-voltage transformer, has a low voltage asymmetry.

It is generally known that, in respect of technical properties, the at least one primary winding 11.1, the at least one first secondary winding 12.1 and the at least one second secondary winding 12.2 are conventionally comparable. Therefore, in order to avoid unnecessary repetitions, the technical properties will be described below preferably in relation to the at least one first secondary winding 12.1, it being possible to transfer this description to the at least one primary winding 11.1 and/or the at least one second secondary winding 12.1 accordingly.

If the at least one first secondary winding 12.1 comprises the first oscillating circuit 12.1.S, transmission behavior of the high-voltage transformer 10 conventionally matches transmission behavior of the real high-voltage transformer. The at least one first secondary winding 12.1 typically comprises the first oscillating circuit 12.1.S in that the at least one first secondary winding 12.1 behaves in particular like an electric circuit with the first leakage inductance $L_{o1}$ and with the first winding capacitance $C_{W1}$. In other words, the first leakage inductance $L_{o1}$ and the first winding capacitance $C_{W1}$ conventionally generate the first oscillating circuit 12.1.S of the at least one first secondary winding 12.1.

The reference numerals $C_{W1}$, $C_{W2}$, $L_{o1}$, $L_{o2}$ are likewise symbols $C_{W1}$, $C_{W2}$, $L_{o1}$, $L_{o2}$ of the corresponding leakage inductances and winding capacitances.

The first resonance frequency is calculated as follows:

$$f_1 = 1/(2*\pi*(L_{o1}*C_{W1})^{(1/2)})$$

If the first resonance frequency matches the second resonance frequency, the following equation is preferably satisfied:

$$L_{o1}*C_{W1} = L_{o2}*C_{W2}$$

If the first winding capacitance $C_{W1}$ differs in value from the second winding capacitance $C_{W2}$, the following equation is preferably satisfied:

$$C_{W1} != C_{W2}$$

If the first leakage inductance $L_{o1}$ differs in value from the second leakage inductance $L_{o2}$, the following equation is preferably satisfied:

$$L_{o1} != L_{o2}$$

To match in value or correspond in value means in particular that a first value, which is a first non-negative real number, is the same as a second value, which is a second non-negative real number. In other words, the two values are the same. If, for example, the first resonance frequency is 100 kHz as the first value and the second resonance frequency is 100 kHz as the second value, then the first value and the second value match.

To differ in value means in particular that the first value is greater or smaller than the second value.

If, for example, the first winding capacitance CW1 is 200 nF as the first value and the second winding capacitance CW2 is 100 nF as the second value, then the first value and the second value differ because the second value is greater than the first value.

Figure 2:
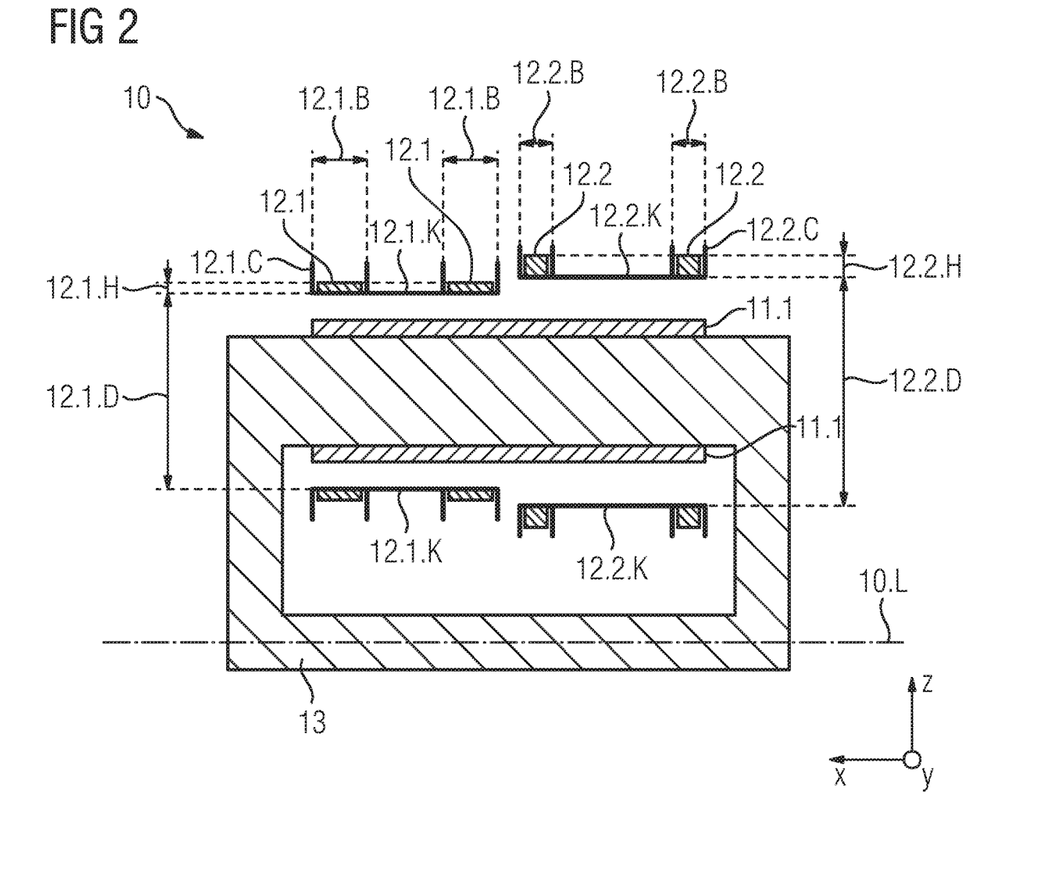
FIG. 2 shows a schematic cross-section through a high-voltage transformer in a second example embodiment.

FIG. 2 shows the high-voltage transformer 10 in a schematic cross-section. The high-voltage transformer 10 has a transformer core 13, wherein the at least one primary winding 11.1, the at least one first secondary winding 12.1 and the at least one second secondary winding 12.2 are wound around the transformer core 13 in accordance with an outer winding. Typically, in accordance with the outer winding, the at least one primary winding 11.1, the at least one first secondary winding 12.1 and the at least one second secondary winding 12.2 are wound around the same leg of the transformer core 13. Alternatively it is conceivable for the at least one primary winding 11.1, the at least one first secondary winding 12.1 and the at least one second secondary winding 12.2 to be wound around two or three different legs of the transformer core 13. The transformer core 13 conventionally has a magnetic core made of a magnetically soft material with high magnetic permeability.

The high-voltage transformer 10 has a primary coil body and a secondary coil body. The primary coil body and/or the secondary coil body are typically not-metallic, in particular are formed from plastic. The primary coil body and the secondary coil body typically act as insulation between the windings 11.1, 12.1, 12.2 and the transformer core 13. The primary coil body and/or the secondary coil body preferably have little, particularly advantageously no, effect on the leakage inductances $L_{o1}$, $L_{o2}$ and the winding capacitances CW1, CW2. The primary coil body and further typical components of the high-voltage transformer 10 are not shown in FIG. 2 for reasons of clarity.

The secondary coil body has a first secondary coil half 12.1.K and a second secondary coil half 12.2.K. The first secondary coil half 12.1.K and the second secondary coil half 12.2.K can be formed as part of a single secondary coil body or as two parts of the secondary coil body that are separate from each other, as shown in FIG. 2. In other words, the first secondary coil half 12.1.K can be structurally separate from the second secondary coil half 12.2.K.

The first secondary coil half 12.1.K has the at least one first secondary winding 12.1 and the second secondary coil half 12.2.K has the at least one second secondary winding 12.2. The primary coil body and the secondary coil body, in particular the first secondary coil half 12.1.K and the second secondary coil half 12.2.K, typically act as a holding device for the respectively arranged windings 11.1, 12.1, 12.2. For example, the at least one first secondary winding 12.1 is mechanically supported via the first secondary coil half 12.1.K, while the at least one second secondary winding 12.2 is mechanically supported via the second secondary coil half 12.2.K. In other words, the at least one first secondary winding 12.1 is arranged and/or wound around the first secondary coil half 12.1.K and the at least one second secondary winding 12.2 is arranged and/or wound around the second secondary coil half 12.2.K.

The first secondary coil half 12.1.K and the second secondary coil half 12.2.K are constructed asymmetrically to each other. The asymmetric construction can follow from a mechanical measure and/or be obtained in accordance with a selection of different material for the formation of the windings 12.1, 12.2. The materials typically differ in material characteristics, such as, for example in an electrical and/or magnetic conductivity or capacity.

It is generally known that the asymmetric construction can have a plurality of technical effects, for example:
a variation of the first winding capacitance $C_{W1}$,
a variation of the second winding capacitance $C_{W2}$,
a variation of the first leakage inductance $L_{o1}$,
a variation of the second leakage inductance $L_{o2}$ and/or
any combination of the preceding technical effects.
Alternatively or additionally it is conceivable that, despite a plurality of technical effects, a first technical effect predominates and/or a second technical effect, in particular in an ideal environment, is negligible.

Furthermore, it is conceivable that various measures, in particular one of the mechanical measures is combined with the selection of the different materials for the formation of the windings 12.1, 12.2 in any way such that the first resonance frequency and the second resonance frequency match, wherein the first winding capacitance $C_{W1}$ and the second winding capacitance $C_{W2}$ differ in value and wherein the first leakage inductance $L_{o1}$ and the second leakage inductance $L_{o2}$ differ in value.

Typically, due to the asymmetry of the first secondary coil half 12.1.K and the second secondary coil half 12.2.K, in particular a spatial position of the at least one first secondary winding 12.1 differs from a spatial position of the at least one second secondary winding 12.2, typically due to the mechanical measure. The spatial position of the at least one first secondary winding 12.1 has, for example, a position, an orientation, a winding height and/or a diameter. For example, the spatial position of the at least one first secondary winding 12.1, relative to the transformer core 13, influences a leakage flux, wherein the leakage flux typically correlates with the first leakage inductance $L_{o1}$. Alternatively or additionally, the first winding capacitance $C_{W1}$ typically varies if the spatial position of the at least one first secondary winding 12.1 is changed in relation to itself, in particular if the winding height of the at least one first secondary winding 12.1 is varied.

In this example embodiment a first diameter 12.1.D of the at least one first secondary winding 12.1 is smaller than a second diameter 12.2.D of the at least one second secondary winding 12.2, so that the first leakage inductance L61 is smaller than the second leakage inductance $L_{o2}$. In this case a leakage flux, due to the at least one first secondary winding 12.1, in particular the losses, is smaller compared to a leakage flux due to the at least one second secondary winding 12.2. If the first diameter 12.1.D differs from the second diameter 12.2.D, for example the spatial position of the at least one first secondary winding 12.1 is different in relation to the spatial position of the at least one second secondary winding 12.2.

In this example embodiment the at least one first secondary winding 12.1 is arranged in a first chamber 12.1.C of the first secondary coil half 12.1.K, wherein the at least one second secondary winding 12.2 is arranged in a second chamber 12.2.C of the second secondary coil half 12.2.K and wherein a first width 12.1.B of the first chamber 12.1.C is greater than a second width 12.2.B of the second chamber 12.2.C, so that the first winding capacitance $C_{W1}$ is greater than the second winding capacitance $C_{W2}$. The first chamber 12.1.C and the second chamber 12.2.C typically act in such a way that the at least one first secondary winding 12.1 is mechanically held and/or fixed relative to the first secondary coil half 12.1.K and also the at least one second secondary winding 12.2 is mechanically held and/or fixed relative to the second secondary coil half 12.2.K. Each chamber 12.1.C, 12.2.C conventionally has webs, with the webs together with the secondary coil body produce a u-shaped profile of the chambers 12.1.C, 12.2.C. Alternatively or additionally, the chambers 12.1.C, 12.2.C can have an o-shaped profile and/or, without the webs, no profile at all.

The high-voltage transformer 10 has at least one longitudinal axis 10.L, with the longitudinal axis 10.L being designed parallel to the x-axis in this example embodiment. In this example embodiment the first width 12.1.B and the second width 12.2.B describe, in particular, a width of the chambers 12.1.C, 12.2.C along the x-axis. The first diameter 12.1.D and the second diameter 12.2.D are parallel to the z-axis in this example embodiment.

Typically, the at least one first secondary winding 12.1 and the at least one second secondary winding 12.2 have an equal number of winding wires. In particular, the at least one first secondary winding 12.1 and the at least one second secondary winding 12.2 have a plurality of winding wires. The winding wires are typically made of copper.

If the first width 12.1.B is greater than the second width 12.2.B, a first winding height 12.1.H of the at least one first secondary winding 12.1 is conventionally smaller than a second winding height 12.2.H of the at least one second secondary winding 12.2. If the first winding height 12.1.H of the at least one first secondary winding 12.1 is smaller than the second winding height 12.2.H of the at least one second secondary winding 12.2, the first leakage inductance $L_{o1}$ is conventionally smaller than the second leakage inductance $L_{o2}$. The first leakage inductance $L_{o1}$ and the second leakage inductance $L_{o2}$ conventionally differ therefore if the first width 12.1.B differs from the second width 12.2.B. A winding width is typically indirectly proportional to the winding height 12.1.H, 12.2.H.

A particularly advantageous example embodiment can be if the first winding capacitance $C_{W2}$ and the second winding capacitance $C_{W2}$ and also the first leakage inductance $L_{o1}$ and the second leakage inductance $L_{o2}$ differ in value because the first width 12.1.B is greater than the second width 12.2.B and because the first diameter 12.1.D is smaller than the second diameter 12.2.D.

In a further example embodiment different materials are selected for the formation of the windings 12.1, 12.2. A winding wire of the at least one first secondary winding 12.1 differs from a winding wire of the at least one second secondary winding 12.1, in this case according to at least one parameter from the following list:
a thickness of the winding wire,
a thickness of an enamel insulation layer of the winding wire,
a dielectric constant of the enamel insulation layer of the winding wire. In this case the selection of the different materials causes the first winding capacitance $C_{W1}$ and also the second winding capacitance $C_{W2}$ to differ.

Figure 3:
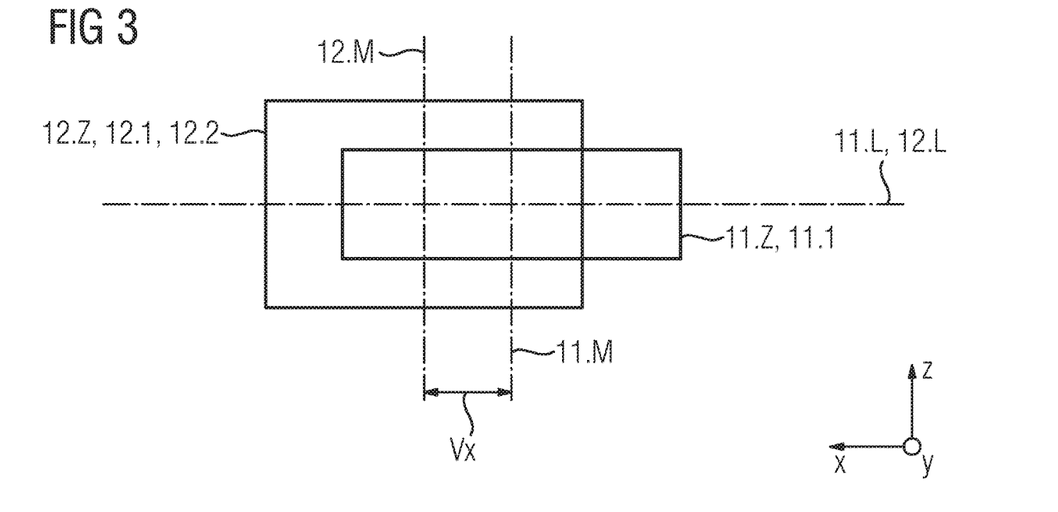
FIG. 3 shows a schematic asymmetric structure of a high-voltage transformer in a third example embodiment.

FIG. 3 shows the high-voltage transformer 10, in particular a spatial position of the at least one primary winding 11.1, a spatial position of the at least one first secondary winding 12.1 and a spatial position of the at least one second secondary winding 12.2 relative to each other, in a pattern according to an asymmetric construction.

The at least one primary winding 11.1 forms a first cylinder 11.Z having a first longitudinal axis 11.L, wherein the at least one first secondary winding 12.1 and the at least one second secondary winding 12.2 together form a second cylinder 12.Z having a second longitudinal axis 12.L. The imaginary formation of the cylinder serves in particular to represent the position relative to each other. Basically, the at least one primary winding 11.1, the at least one first secondary winding 12.1 and/or the at least one second secondary winding 12.2 can be cylindrical.

The first longitudinal axis 11.L is formed parallel to the second longitudinal axis 12.L and also to the x-axis shown in FIG. 3. In this example embodiment the first longitudinal axis 11.L is congruent with the second longitudinal axis 12.L.

The first cylinder 11.Z has a first center line 11.M, wherein the second cylinder 12.Z has a second center line 12.M. The first center line 11.M and the second center line 12.M each identify a center of the first cylinder 11.Z or of the second cylinder 12.Z.

The first cylinder 11.Z is arranged offset along the first longitudinal axis 11.L relative to the second cylinder 12.Z, in particular about the offset Vx. In other words, the first center line 11.M is shifted along the first longitudinal axis 11.L, in particular along the x-axis, about the offset Vx relative to the second center line 12.M. Basically it is conceivable that the first cylinder 11.Z is shifted along the z-axis and/or along the y-axis relative to the second cylinder. In other words, the first cylinder 11.Z can be arranged offset about an offset in each of the spatial directions relative to the second cylinder 12.Z, so that the first cylinder 11.Z is arranged rotated relative to the second cylinder 12.Z. Arranged offset can mean that the first cylinder 11.Z is shifted out of a shared center relative to the second cylinder 12.Z.

If the first cylinder 11.Z is arranged offset relative to the second cylinder 12.Z, the first leakage inductance $L_{o1}$ typically differs in value from the second leakage inductance $L_{o2}$.

Figure 4:
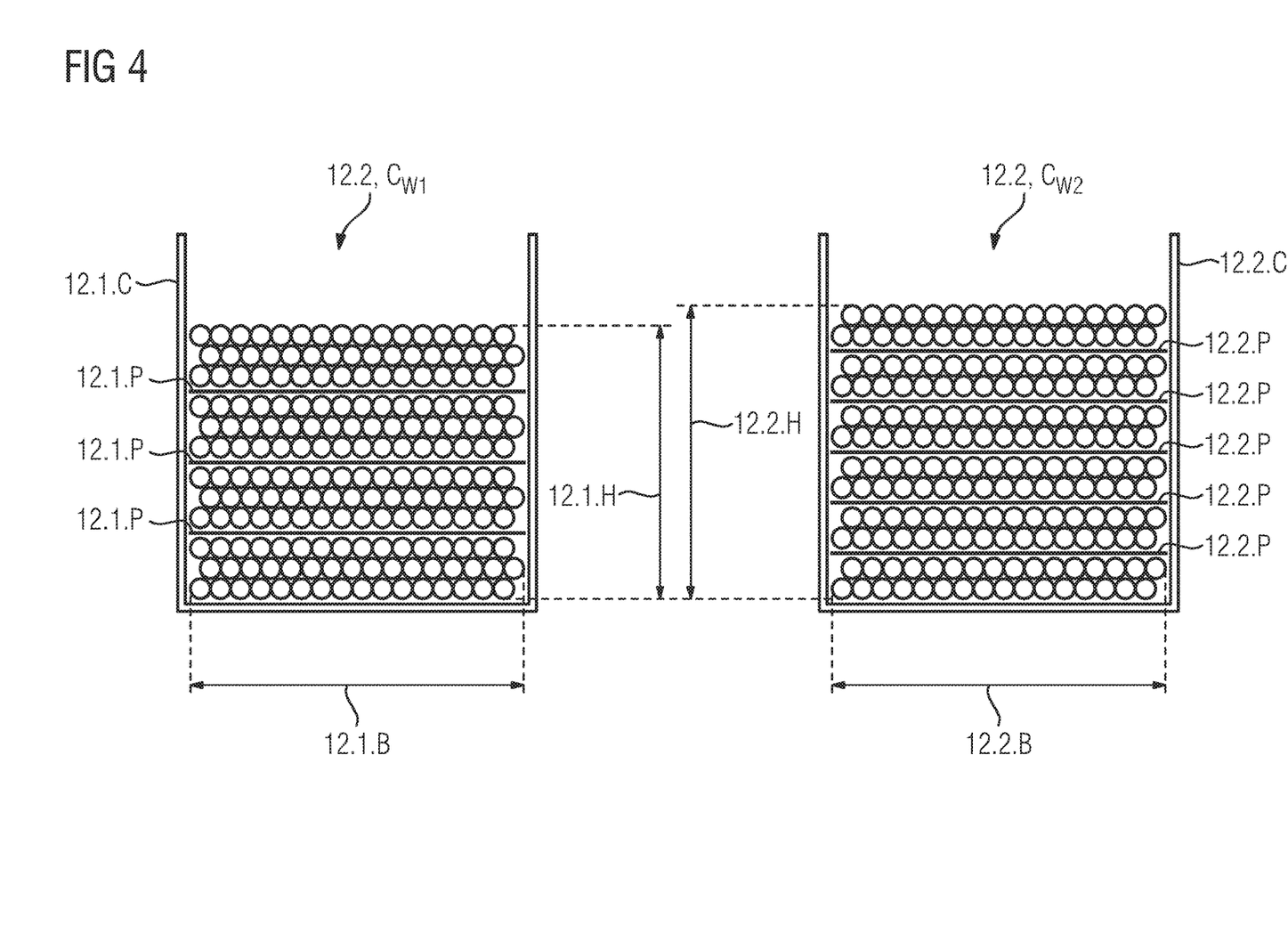
FIG. 4 shows a schematic cross-section through a high-voltage transformer in a fourth example embodiment.

FIG. 4 shows the high-voltage transformer 10, in particular the first chamber 12.1.C and the second chamber 12.2.C, in a schematic cross-section.

The at least one first secondary winding 12.1 is arranged in the first chamber 12.1.C of the first secondary coil half 12.1.K together with at least one first paper insulation layer 12.1.P.

The at least one second secondary winding 12.2 is arranged in the second chamber 12.2.C of the second secondary coil half 12.2.K together with at least one second paper insulation layer 12.2.P.

The first chamber 12.1.C and the second chamber 12.2.C have the u-shaped profile. In contrast to the example embodiment shown in FIG. 2, the first width 12.1.B of the first chamber 12.1.C is equal in value to the second width 12.2.B of the second chamber 12.2.C.

An arrangement of the first paper insulation layer 12.1.P relative to the at least one first secondary winding 12.1 differs from an arrangement of the second paper insulation layer 12.2.P relative to the at least one second secondary winding 12.2. The at least one first secondary winding 12.1 and the at least one second secondary winding 12.2 have the same number of winding wires, wherein the winding wires in this example embodiment are in each case arranged in 12 winding layers in the first chamber 12.1.C and in the second chamber 12.2.C. The first paper insulation layer 12.1.P comprises, for example, three separating layers, while the second paper insulation layer 12.2.P comprises five separating layers, so that the first winding height 12.1.H is smaller than the second winding height 12.2.H. In this example embodiment the first winding capacitance $C_{W1}$ is greater than the second winding capacitance $C_{W2}$. Typically, the winding capacitances $C_{W1}$, $C_{W2}$ are greater, the more winding layers are arranged per separating layer.

Figure 5:
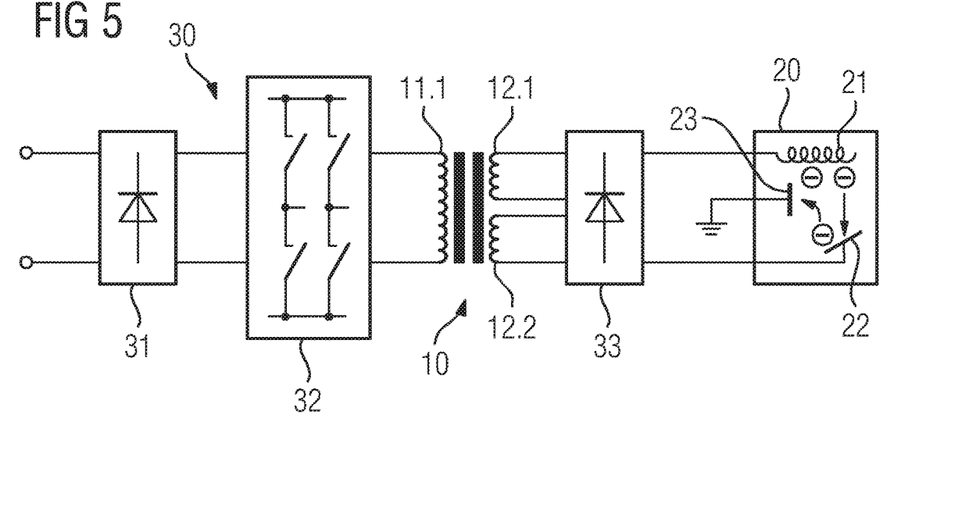
FIG. 5 shows a block diagram of a circuit arrangement in a fifth example embodiment and FIG. 6 shows an X-ray unit in a sixth example embodiment.

FIG. 5 shows a circuit arrangement 30 in a block diagram. The circuit arrangement 30 has the high-voltage transformer 10 and the X-ray tube 20. The X-ray tube 20 has a cathode 21 and an anode 22. The at least one first secondary winding 12.1 is electrically connected to the cathode 21 and the at least one second secondary winding 12.2 is electrically connected to the anode 22. A power inlet circuit 31 and an inverter circuit 32 are interconnected at an input side of the high-voltage transformer 10. The inverter circuit 32 can have a half-bridge circuit and/or a full-bridge circuit. A rectifier 33 is interconnected between the high-voltage transformer 10 and the X-ray tube 20 on an output side. The rectifier 33 can be a voltage doubler rectifier. On a first side the rectifier 33 typically has the differential current 10.IΔ of the high-voltage transformer 10 and/or on a second side, the differential current 20.IΔ of the X-ray tube 20.

In this example embodiment the X-ray tube 20 has a metal central part 23. The differential current 20.IΔ of the X-ray tube 20 is adjusted between the anode 22 and the metal central part 23. In this case the metal central part 23 is typically grounded, over which the differential current 20.IΔ of the X-ray tube 20 flows-off.

Basically it is conceivable for at least one oscillating circuit throttle to be interconnected between the high-voltage transformer 10 and the X-ray tube 20. Advantageously, the first leakage inductance $L_{o1}$ and/or the second leakage inductance $L_{o2}$ can be influenced and/or adjusted via the at least one oscillating circuit throttle.

In a further example embodiment at least one capacitor is interconnected between the high-voltage transformer 10 and the X-ray tube 20, in particular parallel to the at least one first secondary winding 12.1 and/or parallel to the at least one second secondary winding 12.2. Advantageously, the first winding capacitance $C_{W1}$ and/or the second winding capacitance $C_{W2}$ can be influenced and/or adjusted via the at least one capacitor.

Figure 6:
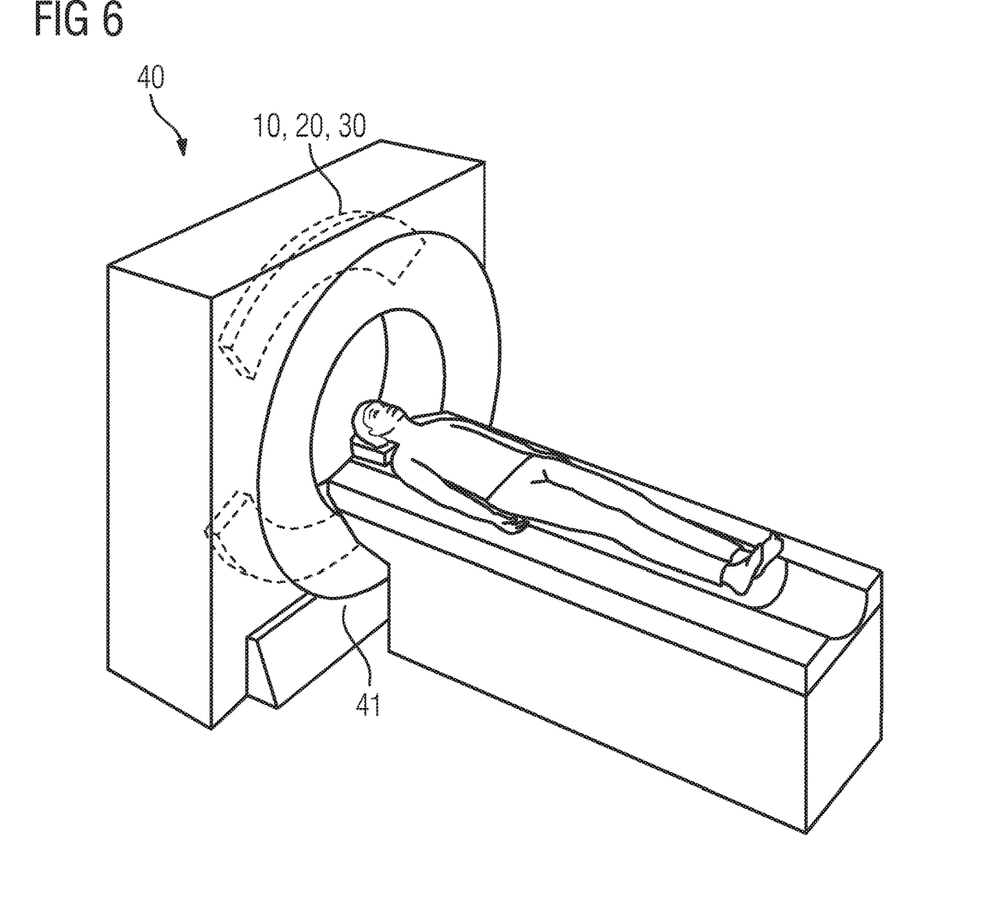

FIG. 6 shows an X-ray unit 40. The X-ray unit 40 has the circuit arrangement 30. In addition to the circuit arrangement 30, the X-ray unit 40 typically has an X-ray detector 41 which can detect X-ray radiation generated at the anode 22. The X-ray unit 40 can be used, for example, for medical imaging, in particular an angiography examination. Basically it is conceivable that non-medical imaging is carried out by the X-ray unit 40.

In this example embodiment the X-ray unit 40 is designed as a computed tomography unit. The computed tomography unit has a patient couch around which the X-ray tube 20 and the X-ray detector 41 are typically mounted so as to rotate. Basically it is conceivable that the high-voltage transformer 10 is constructed in such a way that the at least one primary winding 11.1 is stationary, while the at least one first secondary winding 12.1 and the at least one second secondary winding 12.2 rotate around the patient couch with the X-ray tube 20 and the X-ray detector 41. The high-voltage transformer 10 is used in particular for transmitting power for operation of the X-ray tube 20 and/or of the X-ray detector 41. Basically it is conceivable that data is transmitted via the high-voltage transformer 10.

Although the invention has been illustrated and described and in detail by the preferred example embodiments, it is nevertheless not limited by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A circuit arrangement, comprising:
   an X-ray tube, including a cathode and an anode; and
   a high-voltage transformer, including
      at least one primary winding,
      at least one first secondary winding, including a first oscillating circuit, wherein the first oscillating circuit includes a first leakage inductance and a first winding capacitance, to adjust a first resonance frequency, and
      at least one second secondary winding, including a second oscillating circuit, wherein the second oscillating circuit includes a second leakage inductance and a second winding capacitance, to adjust a second resonance frequency, the first resonance frequency matching the second resonance frequency, the first winding capacitance and the second winding capacitance differing in value and the first leakage inductance and the second leakage inductance differing in value,
   wherein the at least one first secondary winding is electrically connected to the cathode and the at least one second secondary winding is electrically connected to the anode.

2. The circuit arrangement of claim 1, wherein a first load current is adjusted in the at least one first secondary winding during operation, wherein a second load current is adjusted in the at least one second secondary winding, wherein the first load current differs from the second load current by a differential current of the high-voltage transformer, proportional to a differential current of the X-ray tube.

3. The circuit arrangement of claim 2, wherein the at least one primary winding forms a first cylinder having a first longitudinal axis, wherein the at least one first secondary winding and the at least one second secondary winding together form a second cylinder having a second longitudinal axis, wherein the first longitudinal axis is parallel to the second longitudinal axis and wherein the first cylinder is arranged offset relative to the second cylinder along the first longitudinal axis.

4. The circuit arrangement of claim 2, wherein a winding wire of the at least one first secondary winding differs from a winding wire of the at least one second secondary winding according to at least one parameter including:
   a thickness of the winding wire,
   a thickness of an enamel insulation layer of the winding wire, or
   a dielectric constant of the enamel insulation layer of the winding wire.

5. The circuit arrangement of claim 2, wherein a first diameter of the at least one first secondary winding is relatively smaller than a second diameter of the at least one second secondary winding, and the first leakage inductance being relatively smaller than the second leakage inductance.

6. An X-ray unit, comprising:
   an X-ray detector; and
   the circuit arrangement of claim 2.

7. A computed tomography unit, comprising:
   the X-ray unit of claim 6.

8. The circuit arrangement of claim 1, wherein the at least one primary winding forms a first cylinder having a first longitudinal axis, wherein the at least one first secondary winding and the at least one second secondary winding together form a second cylinder having a second longitudinal axis, wherein the first longitudinal axis is parallel to the second longitudinal axis and wherein the first cylinder is arranged offset relative to the second cylinder along the first longitudinal axis.

9. The circuit arrangement of claim 8, wherein a winding wire of the at least one first secondary winding differs from a winding wire of the at least one second secondary winding according to at least one parameter including:
   a thickness of the winding wire,
   a thickness of an enamel insulation layer of the winding wire, or
   a dielectric constant of the enamel insulation layer of the winding wire.

10. The circuit arrangement of claim 1, wherein a winding wire of the at least one first secondary winding differs from a winding wire of the at least one second secondary winding according to at least one parameter including:
    a thickness of the winding wire,
    a thickness of an enamel insulation layer of the winding wire, or
    a dielectric constant of the enamel insulation layer of the winding wire.

11. The circuit arrangement of claim 1, wherein a first diameter of the at least one first secondary winding is relatively smaller than a second diameter of the at least one second secondary winding, and the first leakage inductance being relatively smaller than the second leakage inductance.

12. The circuit arrangement of claim 1, wherein the high-voltage transformer includes a primary coil body and a secondary coil body, wherein the secondary coil body includes a first secondary coil half and a second secondary coil half, wherein the first secondary coil half includes the at least one first secondary winding, wherein the second secondary coil half includes the at least one second secondary winding and wherein the first secondary coil half and the second secondary coil half are constructed asymmetrically to each other.

13. The circuit arrangement of claim 12, wherein the at least one first secondary winding is arranged in a first chamber of the first secondary coil half together with at least one first paper insulation layer, wherein the at least one second secondary winding is arranged in a second chamber of the second secondary coil half together with at least one second paper insulation layer and wherein an arrangement of the first paper insulation layer relative to the at least one first secondary winding differs from an arrangement of the second paper insulation layer relative to the at least one second secondary winding.

14. The circuit arrangement of claim 13, wherein the at least one first secondary winding is arranged in a first chamber of the first secondary coil half, wherein the at least one second secondary winding is arranged in a second chamber of the second secondary coil half and wherein a first width of the first chamber is relatively greater than a second width of the second chamber, the first winding capacitance being relatively greater than the second winding capacitance.

15. The circuit arrangement of claim 12, wherein the at least one first secondary winding is arranged in a first chamber of the first secondary coil half, wherein the at least one second secondary winding is arranged in a second chamber of the second secondary coil half and wherein a first width of the first chamber is relatively greater than a second width of the second chamber, the first winding capacitance being relatively greater than the second winding capacitance.

16. The circuit arrangement of claim 1, wherein the X-ray tube includes a metal central part and wherein a differential current of the X-ray tube is adjustable between the anode and the metal central part during operation.

17. The circuit arrangement of claim 1, wherein at least one oscillating circuit throttle is interconnected between the high-voltage transformer and the X-ray tube.

18. The circuit arrangement of claim 1, wherein at least one capacitor is interconnected between the high-voltage transformer and the X-ray tube.

19. An X-ray unit, comprising:
an X-ray detector; and
the circuit arrangement of claim 1.

20. A computed tomography unit, comprising:
the X-ray unit of claim 19.

* * * * *